United States Patent [19]

Bergmann et al.

[11] Patent Number: 5,650,143
[45] Date of Patent: Jul. 22, 1997

[54] DEODORANT COSMETIC STICK COMPOSITION

[75] Inventors: Wolfgang R. Bergmann, Princeton; Richard T. Murphy, Belle Mead; Linda J. Lancaster, Old Bridge, all of N.J.

[73] Assignee: Church & Dwight Co., Inc., Princeton, N.J.

[21] Appl. No.: 655,140

[22] Filed: May 30, 1996

[51] Int. Cl.$^6$ .................. A61K 7/32; A61K 7/00
[52] U.S. Cl. .............. 424/65; 424/40 D; 424/401; 424/DIG. 5; 512/1
[58] Field of Search ............... 424/65, 400, 401, 424/DIG. 5; 512/1

[56] References Cited

U.S. PATENT DOCUMENTS

| | | | |
|---|---|---|---|
| 4,382,079 | 5/1983 | Marschner | 424/65 |
| 4,440,742 | 4/1984 | Marschner | 424/65 |
| 4,822,602 | 4/1989 | Sabatelli | 424/65 |
| 4,832,945 | 5/1989 | Osipow et al. | 424/65 |

*Primary Examiner*—Shelley A. Dodson
*Attorney, Agent, or Firm*—Irving M. Fishman

[57] ABSTRACT

This invention provides a deodorant cosmetic stick product which has a translucent or transparent light transmitting appearance. The cosmetic stick has a content of ingredients such as propylene glycol, sodium stearate, dimethicone copolyol, Triclosan, Pentadoxynol-200, and water. An invention deodorant cosmetic stick has excellent esthetics when applied underarm, such as smoothness and a comfortable dry feel, and without a visually perceptible residue.

11 Claims, No Drawings

DEODORANT COSMETIC STICK COMPOSITION

CROSS-REFERENCE TO RELATED APPLICATIONS

The subject matter of this patent application is related to that disclosed in copending patent application Ser. No. 08/503,939, filed Jul. 19, 1995; Ser. No. 08/526,269, filed Sep. 13, 1995; and Ser. No. 08/534,819, filed Sep. 27, 1995.

BACKGROUND OF THE INVENTION

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective composition in cosmetic stick form which has a deodorization capacity, and which is capable of consumer acceptability, presents many factors which are unique. Because sodium and potassium bicarbonate have only limited solubility in water, alcohol and other solvents, the preparation of a composition suitable for dispensing in cosmetic stick form has involved many processing obstacles. In addition to the problem of limited solubility, sodium bicarbonate often is incompatible with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low residue deodorant cosmetic stick product.

A recent trend is toward the development of cosmetic sticks which have light transmitting properties, i.e., the cosmetic sticks are translucent or transparent in light transmitting properties, and engender a perceived appearance of purity.

Cosmetic sticks which are soap-based and which have a content of sodium bicarbonate as a deodorant ingredient typically are opaque in appearance. U.S. Pat. No. 4,440,742 describes anhydrous and water-based deodorant cosmetic sticks which contain sodium bicarbonate, and which vary from opaque to transparent in appearance as determined by the proportions of sodium bicarbonate and water, in combination with other ingredients.

There are difficulties associated with the preparation of water-based cosmetic stick products which contain sodium bicarbonate as a deodorant ingredient. Thus, the transparency properties do not have long-term stability. Acceptable degrees of hardness and smoothness are not readily achieved, and an unpleasant cool-wetness is experienced when the cosmetic stick is applied to a skin surface.

There is continuing interest in the development of water-based deodorant cosmetic stick products which have a high degree of consumer acceptance.

Accordingly, it is an object of this invention to provide a cosmetic stick product which is a water-based bicarbonate-free composition having an effective deodorizing content of a bacteriostat ingredient.

It is another object of this invention to provide a deodorant cosmetic stick product having stable transparency and affording a comfortable dry feel when applied to a skin surface.

Other objects and advantages of the present invention shall become apparent from the accompanying description and examples.

DESCRIPTION OF THE INVENTION

One or more objects of the present invention are accomplished by the provision of a deodorant cosmetic stick product with transparency which comprises (1) about 40–70 weight percent of polyhydric alcohol ingredient, (2) about 2–8 weight percent of hydrophilic silicone-polyol clarifier-surfactant ingredient, (3) about 3–10 weight percent of $C_{14}$–$C_{22}$ fatty acid salt ingredient, (4) about 0.01–0.5 weight percent of bacteriostat ingredient, and (5) about 24–64 weight percent of water; wherein the weight ratio of water:silicone polyol ingredients is between about 3–12:1, and wherein the deodorant stick product has a penetration value between about 2–6.

The term "transparency" as employed herein refers to invention cosmetic stick products which have translucent or transparent light transmitting properties.

The term "transparent" refers to a clear body which has the property of transmitting light without appreciable scattering, so that objects beyond are entirely visible.

The term "translucent" refers to a body which is partly transparent. The body admits and diffuses light, so that objects beyond cannot be clearly distinguished.

The term "opaque" refers to a body which is impervious to visible light. An opaque body lacks any degree of transparency.

The polyhydric alcohol ingredient is selected from organic compounds which contain about 2–6 carbon atoms, and about 2–6 hydroxy groups. Illustrative of polyhydric alcohols are ethylene glycol, propylene glycol, trimethylene glycol, butylene glycol, diethylene glycol, dipropylene glycol, glycerin, sorbitol, and the like, and mixtures thereof. Preferred polyhydric alcohols are those which are water-miscible in all proportions such as ethylene glycol, propylene glycol, diethylene glycol, dipropylene glycol, and glycerin.

An essential aspect of a present invention cosmetic stick product is a content of a hydrophilic silicone-polyol clarifier-surfactant ingredient. The silicone-polyol ingredient is selected from a specific structural type of silicone nonionic surfactant polymers, having multiple polyoxyalkylene sidechains which impart hydrophilic properties to the clarifier-surfactant ingredient.

The term "hydrophilic" as employed herein refers to a water-dispersible silicone-polyol ingredient which has a water-solubility of at least about two grams per one hundred grams of water at 25° C.

Illustrative of hydrophilic silicone-polyol clarifier-surfactant ingredients are dimethicone copolyol type of polymers, which include commercial products such as Dow Corning 193, GE SF-1288, Abil B 8847 (Goldschmidt), Alkasil NE 58-50 (Rhone-Poulenc), Amersil DMC-287 (Americol), KF 353A (Shin Etsu), Masil i066D (PPG/Mazer), Silicone Copolymer F-754 (Wacker), Sibwet L-7000 (Union Carbide), and the like; and similar hydrophilic silicone-polyols as listed in the CFTA International Cosmetic Ingredient Dictionary (Fourth Edition), incorporated by reference.

The hydrophilic silicone-polyol clarifier-surfactant ingredient contributes important advantages to a present invention cosmetic stick product. The silicone-polyol ingredient enhances the transparency of the cosmetic stick, and stabilizes the degree of clarity over an extended period of six months or longer under normal storage and usage conditions.

The silicone-polyol ingredient has a gelling effect, and increases the hardness of the cosmetic stick. The silicone polyol ingredient also functions as a compatibility enhancing agent, which improves the homogeneity of the diverse inorganic and organic constituents in the solid matrix.

Other advantages of the silicone-polyol ingredient are apparent when an invention cosmetic stick product is applied to an underarm skin area. There is ease and smoothness of application, because of the physical glidability of the silicone-polyol ingredient. There is an improvement in other esthetic values as well, such as a reduction in the unpleasant cool-wetness typical of cosmetic stick usage. The silicone-polyol ingredient also is a contributing factor to the absence of a visually perceptible residue as characteristic of a present invention cosmetic stick product after application.

Because of the absence of a bicarbonate salt ingredient, a present invention cosmetic stick product can exhibit excellent clarity and dimensional stability, and provide improved esthetic appearance and "feel".

A present invention cosmetic stick product includes a hardener ingredient, which preferably is selected from $C_{14}$–$C_{22}$ fatty acid salts. Suitable fatty acid salts include alkali metal, alkaline earth metal, aluminum, ammonium and amine salts of fatty acids such as myristic, palmitic, stearic, behenic, oleic, linoleic, linolenic, and the like, and mixtures thereof. Illustrative of specific fatty acid salts are sodium stearate, potassium stearate, aluminum monostearate, sodium oleate, sodium palmitate, sodium behenate, diethylamine stearate, triethylamine stearate, triethylamine oleate, and the like.

A present invention cosmetic stick product also includes between about 0.01–0.5 weight percent, preferably about 0.1–0.4 weight percent, of a bacteriostat ingredient. The bacteriostat functions as a deodorant by preventing bacterial generation of malodorous degradation byproducts from perspiration. Typical bacteriostatic compounds include Triclosan (Ciba-Geigy), Chloracel (Reheis Chemical Company), zinc phenolsulfonate, dichloro-m-xylenol, sodium N-lauroyl sarcosine, and the like.

A present invention cosmetic stick product can contain one or more optional ingredients such as clarifying agents, antiperspirants, fragrances, colorants, and the like.

Between about 0.5–5 weight percent of a clarifying agent can be included as an optional ingredient. Suitable clarifying agents include Pentadoxynol-200 (RTD Chemicals Corp.), tetra(hydroxypropyl)diamine (Quadrol, BASF), 2-amino-2-methylpropanol (AMP, Angus Chemical Company), 2-amino-2-hydroxymethyl-1,3-propanediol (Tromethamine, Sigma Chemical Company), and the like.

Between about 0.1–3 weight percent of a fragrance can be included as an optional ingredient. The selected fragrance ingredient is one which does not adversely affect the clarity of the cosmetic stick product, and preferably which contributes an odorant masking effect. Fragrances typically are organic compounds of specific type structures, which include phenolic materials, essential oils, synthetic oils, aldehydes and ketones, polycyclic compounds, esters, and alcohols. Specific fragrances are illustrated by linalyl acetate, isopropyl myristate, cedryl acetate, myrcenyl acetate, and other compounds such as those listed in U.S. Pat. No. 5,114,717; incorporated by reference.

Between about 0.005–0.0025 weight percent of a colorant can be included as an optional ingredient. Typical colorants are exemplified by FD&C-type dyes and lakes as illustrated in the Examples.

A present invention deodorant cosmetic stick product can be produced by blending the ingredients in a prescribed order of addition.

In a general procedure, the silicone-polyol, fatty acid salt, bacteriostat and optional ingredients are added to propylene glycol with heating to form a solution. The propylene glycol solution then is blended with water at about 90° C. to form a homogeneous liquid medium. The warm liquid medium is poured into molds, and the molded units are cooled to room temperature to form rigid structures.

The hardness of a present invention cosmetic stick can have a value which varies in the range between about 2–6, and preferably is in the range between about 2.3–3.3.

The penetration values (in millimeters) of the cosmetic stick products described herein are measured with a Universal Penetrometer, Model TS-73510 AN-2 (Precision Scientific Inc.).

The penetration values are obtained by following a standardized procedure in accordance with ASTM Method D217-94.

The following examples are further illustrative of the present invention. The components and specific ingredients are presented as being typical, and various modifications can be derived in view of the foregoing disclosure within the scope of the invention.

EXAMPLE I

This Example illustrates the preparation of a translucent deodorant cosmetic stick product in accordance with the present invention.

| Ingredients | Weight percent |
| --- | --- |
| Part 1 | |
| D.I. water | 35.00 |
| Part 2 | |
| propylene glycol | 50.27 |
| Irgasan DP300[1] | 0.28 |
| Dow Corning 193[2] | 4.00 |
| Part 3 | |
| Clarit PDP-200[3] | 2.50 |
| OP-100V[4] | 6.00 |
| Part 4 | |
| D&C Green #5 (0.1% solution) | 0.50 |
| fragrance[5] | 1.45 |

[1] Triclosan (Ciba-Geigy).
[2] Hydrophilic dimethicone copolyol.
[2] Pentadoxynol-200 (RTD Chemicals Corp.).
[4] Sodium stearate (RTD Chemicals Corp.).
[5] Sobica Deofresh RH 1160 Mod (Takasago).

The triclosan and dimethicone copolyol are added to the propylene glycol, and the mixture is heated to 90° C. The Part 3 ingredients are added to the propylene glycol, and heating at 90°–105° C. is maintained until a solution is formed.

The propylene glycol solution and water are blended, and the colorant and fragrance ingredients are blended with the liquid medium (65°–70° C.).

The fluid blend is poured into Plastek 2 oz. bottom-fill cosmetic stick containers. The container contents are cooled to a room temperature solid stick over a period of 45 minutes. The solid stick is translucent in light transmitting appearance, and has an average hardness value of 2.4 millimeters (ASTM Method 217-94).

EXAMPLE II

This Example illustrates the preparation of a transparent deodorant cosmetic stick product in accordance with the present invention.

| Ingredients | Weight percent |
|---|---|
| Part 1 | |
| D.I. water | 40.00 |
| Part 2 | |
| propylene glycol | 41.77 |
| dipropylene glycol | 3.00 |
| Irgasan DP300[1] | 0.28 |
| Dow Corning 193[2] | 5.00 |
| Part 3 | |
| Clarit PDP-200[3] | 3.00 |
| OP-100V[4] | 5.00 |
| Part 4 | |
| D&C Green #5 (0.1% solution) | 0.50 |
| fragrance[5] | 1.45 |

[1]Triclosan (Ciba-Geigy).
[2]Hydrophilic dimethicone copolyol.
[3]Pentadoxynol-200 (RTD Chemicals Corp.).
[4]Sodium stearate (RTD Chemicals Corp.).
[5]Sobica Deofresh RH 1160 Mod (Takasago).

The ingredients are blended in the manner described in Example I to form a batch of packaged cosmetic stick products.

The solid stick is transparent in light transmitting appearance, and has an average hardness value of 2.9 millimeters (ASTM Method D217-94).

EXAMPLE III

This Example illustrates the preparation of a translucent deodorant cosmetic stick product in accordance with the present invention.

| Ingredients | Weight percent |
|---|---|
| Part 1 | |
| D.I. water | 35.00 |
| Part 2 | |
| propylene glycol | 50.27 |
| Irgasan DP300[1] | 0.28 |
| GE SF-1288[2] | 4.00 |
| Part 3 | |
| Clarit PDP-200[3] | 2.50 |
| OP-100V[4] | 6.00 |

| Ingredients | Weight percent |
|---|---|
| Part 4 | |
| D&C Green #5 (0.1% solution) | 0.50 |
| fragrance[5] | 1.45 |

[1]Triclosan (Ciba-Geigy).
[2]Hydrophilic dimethicone copolyol.
[3]Pentadoxynol-200 (RTD Chemicals Corp.).
[4]Sodium stearate (RTD Chemicals Corp.).
[5]Sobica Deofresh RH 1160 Mod (Takasago).

The ingredients are blended in the manner described in Example I to form a batch of packaged cosmetic stick products.

The solid stick is translucent in light transmitting appearance, and has an average hardness value of 2.4 millimeters (ASTM Method D217-94).

EXAMPLE IV

This Example illustrates the preparation of a transparent deodorant cosmetic stick product with an increased bicarbonate content in accordance with the present invention.

| Ingredients | Weight percent |
|---|---|
| Part 1 | |
| D.I. water | 42.00 |
| Part 2 | |
| propylene glycol | 37.77 |
| glycerin | 5.00 |
| Irgasan DP300[1] | 0.28 |
| GE SF-1288[2] | 4.00 |
| Part 3 | |
| Clarit PDP-200[3] | 4.00 |
| OP-100V[4] | 5.00 |
| Part 4 | |
| D&C Green #5 (0.1% solution) | 0.50 |
| fragrance[5] | 1.45 |

[1]Trichlosan (Ciba-Geigy).
[2]Hydrophilic dimethicone copolyol.
[3]Pentadoxynol-200 (RTD Chemicals Corp.).
[4]Sodium stearate (RTD Chemicals Corp.).
[5]Sobica Deofresh RH 1160 Mod (Takasago).

The ingredients are blended in the manner described in Example I to form a batch of packaged cosmetic stick products.

The solid stick is transparent in light transmitting appearance, and has an average hardness value of 3.1 millimeters (ASTM Method D217-94).

What is claimed is:

1. A deodorant cosmetic stick product with transparency which comprises (1) about 40–70 weight percent of polyhydric alcohol ingredient, (2) about 2–8 weight percent of hydrophilic silicone-polyol clarifier-surfactant ingredient, (3) about 3–10 weight percent of $C_{14}$–$C_{22}$ fatty acid salt ingredient, (4) about 0.01–0.5 weight percent of bacteriostat ingredient, (5) about 24–64 weight percent of water, and (6) about 0.5–5 weight percent of clarifying agent; wherein the weight ratio of water:silicone-polyol ingredients is between about 3–12:1, and wherein the deodorant stick product has a penetration value between about 2–6.

2. A deodorant stick product in accordance with claim 1 which is translucent.

3. A deodorant stick product in accordance with claim 1 which is transparent.

4. A deodorant stick product in accordance with claim 1 wherein the polyhydric alcohol ingredient is ethylene glycol, propylene glycol, diethylene glycol, dipropylene glycol, glycerin, or any mixture thereof.

5. A deodorant stick product in accordance with claim 1 wherein the clarifier-surfactant ingredient has a water-solubility of at least about two grams per one hundred grams of water at 25° C.

6. A deodorant stick product in accordance with claim 1 wherein the clarifier-surfactant ingredient is dimethicone copolyol.

7. A deodorant stick product in accordance with claim 1 wherein the fatty acid salt ingredient is a sodium, potassium, ammonium or amine salt or any mixture thereof.

8. A deodorant stick product in accordance with claim 1 wherein the bacteriostat is Triclosan.

9. A deodorant stick product in accordance with claim 1 which contains between about 0.5–5 weight percent of Pentadoxynol-200 clarifying agent.

10. A deodorant stick product in accordance with claim 1 which additionally contains between about 0.1–3 weight percent of fragrance.

11. A deodorant stick product in accordance with claim 1 which has a penetration value between about 2.3–3.3.

* * * * *